(12) United States Patent  
Jamal-Syed et al.

(10) Patent No.: US 9,288,661 B2
(45) Date of Patent: Mar. 15, 2016

(54) METHODS AND APPARATUSES FOR PERSONALIZED DEVICE USAGE

(75) Inventors: Shaheer Jamal-Syed, Shanghai (CN); Daniel Vahlne, Stockholm (SE)

(73) Assignee: Telefonaktiebolaget L M Ericsson (Publ), Stockholm (SE)

( * ) Notice: Subject to any disclaimer, the term of this patent is extended or adjusted under 35 U.S.C. 154(b) by 149 days.

(21) Appl. No.: 14/122,054

(22) PCT Filed: May 31, 2011

(86) PCT No.: PCT/EP2011/058959
§ 371 (c)(1),
(2), (4) Date: Nov. 25, 2013

(87) PCT Pub. No.: WO2012/163408
PCT Pub. Date: Dec. 6, 2012

(65) Prior Publication Data
US 2014/0099899 A1  Apr. 10, 2014

(51) Int. Cl.
| | |
|---|---|
| *H04W 24/00* | (2009.01) |
| *H04W 8/20* | (2009.01) |
| *H04L 29/06* | (2006.01) |
| *H04W 4/00* | (2009.01) |
| *H04L 29/08* | (2006.01) |

(52) U.S. Cl.
CPC ........... *H04W 8/205* (2013.01); *H04L 63/0492* (2013.01); *H04L 67/306* (2013.01); *H04W 4/00* (2013.01); *H04W 4/005* (2013.01); *H04W 4/008* (2013.01)

(58) Field of Classification Search
CPC ..... H04W 64/00; H04W 40/20; H04W 4/008; H04M 1/72572; H04M 2242/30; H04M 3/42348

USPC ............ 455/456.1, 456.3, 414.2, 414.3, 41.2
See application file for complete search history.

(56) References Cited

U.S. PATENT DOCUMENTS

| | | | |
|---|---|---|---|
| 7,734,299 B2 * | 6/2010 | Panabaker et al. ......... 455/456.1 |
| 7,970,911 B2 * | 6/2011 | Blatherwick et al. ......... 709/227 |
| 8,504,068 B2 * | 8/2013 | Panabaker et al. ......... 455/456.1 |
| 2003/0220765 A1 | 11/2003 | Overy et al. |
| 2009/0254416 A1 | 10/2009 | Nomula |
| 2013/0131845 A1 * | 5/2013 | Guilleminot .................... 700/83 |

(Continued)

OTHER PUBLICATIONS

Beach et al., "WhozThat? Evolving an Ecosystem for Context-Aware mobile Social Networks." IEEE Network. IEEE Service Center. vol. 22, No. 4. Jul. 1, 2008. New York, NY.

*Primary Examiner* — Sonny Trinh
(74) *Attorney, Agent, or Firm* — Patent Portfolio Builders, PLLC (57) ABSTRACT

Methods and arrangements in a first primary device (200) and a secondary device (208), respectively, for enabling personalized usage of the secondary device by a user of the first primary device. The primary device (200) receives (3:1) triangulation information from the secondary device (208) comprising signal strength measurements of signals transmitted from a set of devices (202a-c) associated with the first primary device and forming a limited area (206) of proximity to the first primary device. When the first primary device determines (3:2) that the secondary device is located within the limited area, based on the received triangulation information, it sends (3:4) identity information of the first user to the secondary device. Functions and settings in the secondary device are then adapted (3:6) to the first user, based on the received identity information, to provide personalized usage of the secondary device by the first user.

20 Claims, 4 Drawing Sheets

(56) References Cited

U.S. PATENT DOCUMENTS

| | | | |
|---|---|---|---|
| 2013/0210395 A1* | 8/2013 | Hatami et al. | 455/414.1 |
| 2013/0342426 A1* | 12/2013 | Panabaker et al. | 345/1.3 |
| 2014/0128103 A1* | 5/2014 | Joao et al. | 455/456.3 |
| 2014/0200024 A1* | 7/2014 | Mueck | 455/456.1 |
| 2014/0341201 A1* | 11/2014 | Ibrahim et al. | 370/338 |

* cited by examiner

METHODS AND APPARATUSES FOR PERSONALIZED DEVICE USAGE

TECHNICAL FIELD

The invention relates generally to methods and apparatuses for enabling personalized usage of a device with reduced user efforts.

BACKGROUND

In recent years, the range of devices capable of wireless communication has greatly increased to encompass a huge number of different device types with a variety of different functions and purposes. For example, devices that previously had no abilities for communication have now been equipped with such functionality for remote and/or short range wireless communication, which is used e.g. for providing or retrieving information. Medical devices are an example of such devices, which have sensors with ability to measure various physical parameters of a user, e.g. temperature, blood pressure and heartbeat, to be reported to a central node for medical surveillance. Other examples include cameras capable of communicating with other devices or servers for exchanging pictures, e.g. for uploading captured pictures to a central storage node, and E-books, also referred to as tablets, enabling users to access books and other publications over the Internet, e.g. by subscription.

Thus, there is a growing need for devices, or "gadgets", which can be connected to the Internet for downloading or uploading information and media, e.g. in fields such as health, transportation, finance, retail, and so forth. So-called "M2M" (Machine-to-Machine) devices have also become increasingly common on the market for automatic communication between nodes without user interaction. In the following description, the term "device" is used for short to represent any equipment capable of wireless communication, at least short range communication.

Further, communication devices can typically be adapted to specific users or owners wanting their own personal settings and functions, to provide personalized usage of the device. In this description, the term "personalized" represents any adaptation of a device to a specific user or owner, e.g. in terms of settings, functions and availability of stored data, as well as for uploading information and media to a central server based on user credentials. For example, a camera can be adapted to a particular user by various settings and also by making certain pictures captured or otherwise acquired by the camera available to that user only and no-one else. The camera may also accordingly upload captured pictures to a specific storage associated with the current user. In further examples, a media player may have personal play lists, a medical device may have personal medical data stored, a vehicle unit may have personal settings of certain car functions, and so forth.

It is also desirable sometimes to share a personalized device with another user, and to change the personalization accordingly to become adapted to the other user instead. This can be accomplished e.g. by means of a login procedure when the user inputs his user identity and a password to make the device adapt its settings and functions to the logged-in user. For example, a camera, a game console or a media player may be shared by plural friends or family members when it is desirable for each user to use the device in a personally adapted condition.

Figure 1:
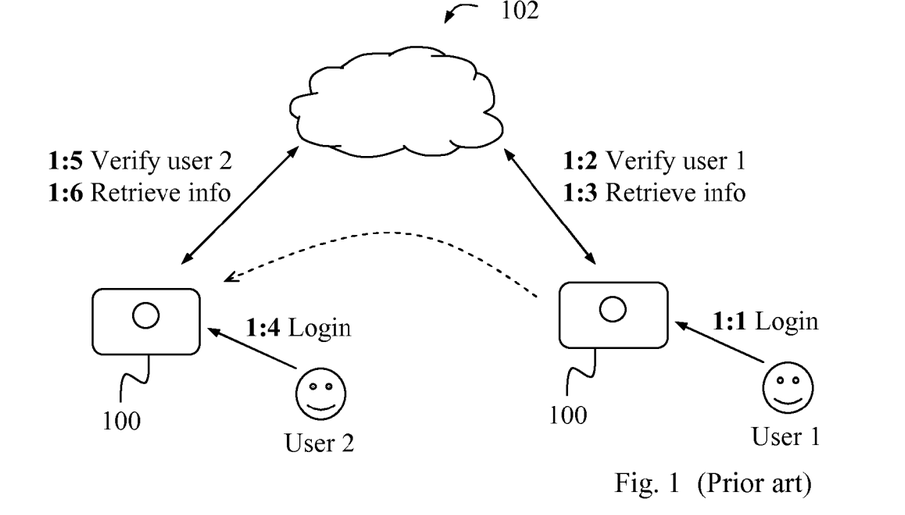
FIG. 1 is a communication overview illustrating how a communication device can be personalized for different users, according to the prior art.

FIG. 1 illustrates an example with a camera 100 which may be capable of communicating with a network 102, e.g. the Internet. A first user "1" logs in to the camera in a first shown action 1:1, which results in some adaptation locally of the camera, e.g. according to a predefined user profile or the like. In some cases, the camera 100 may also verify the user with the network 102, if required, in an action 1:2 and may further retrieve certain user-specific information from the network, in a further action 1:3, as a basis for personalization of the camera.

A dashed arrow illustrates that the camera 100 is handed over to another user "2" who logs in to the camera instead of user 1 in a similar manner, in a next action 1:4. Accordingly, the camera 100 is personalized and adapted for the new user, possibly after another verification in action 1:5 and retrieving of user-specific information from the network in a further action 1:6.

However, there are some drawbacks associated with this known procedure and others. Firstly, the users are required to log in to the camera 100 in order to bring about the proper personalization, which is cumbersome and may not even be possible in some devices. Secondly, the security may be deemed insufficient in this procedure, e.g. when it is possible for an intruder to break a login barrier, if used, and when it is not possible to perform verification and authentication of the current user with the network, such as devices not having functionality therefor and not being registered in the network.

SUMMARY

It is an object of the invention to address at least some of the problems and shortcomings outlined above. It is possible to achieve these objects and others by using a method and an arrangement as defined in the attached independent claims.

According to one aspect, a method is provided in a first primary device for enabling personalized usage of a secondary device by a first user of the first primary device. In this method, the first primary device receives triangulation information from the secondary device. The received triangulation information comprises signal strength measurements by the secondary device of signals transmitted from a set of devices associated with the first primary device and forming a limited area of proximity to the first primary device.

The first primary device then determines whether the secondary device is located within the above limited area based on the received triangulation information, and establishes a connection with the secondary device when the latter is determined to be located within the limited area. The first primary device also sends identity information of the first user to the secondary device, using the established connection, as a basis for adapting functions and settings in the secondary device to provide personalized usage of the secondary device by the first user.

According to another aspect, a method is provided in a secondary device for enabling personalized usage of the secondary device by a first user of a first primary device. In this method, the secondary device sends triangulation information to the first primary device as a basis for determining whether the secondary device is located within said limited area. The triangulation information comprises signal strength measurements performed by the secondary device of signals transmitted from a set of devices associated with the first primary device and forming a limited area of proximity to the first primary device.

When determined to be located within the limited area, the secondary device establishes a connection with the first primary device and receives identity information of the first user from the first primary device. The secondary device then adapts functions and settings in the secondary device, based on the received identity information of the first user, to provide personalized usage of the secondary device by the first user.

According to another aspect, an arrangement is provided in a first primary device operable for enabling personalized usage of a secondary device by a first user of the first primary device. The arrangement in the first primary device comprises a communication module configured to receive triangulation information from the secondary device. The received triangulation information comprises signal strength measurements performed by the secondary device of signals transmitted from a set of devices associated with the first primary device and forming a limited area of proximity to the first primary device. This arrangement further comprises a logic module configured to determine whether the secondary device is located within said limited area based on the received triangulation information.

The communication module in the first primary device is further configured to establish a connection with the secondary device when the latter is determined to be located within the limited area, and to send identity information of the first user to the secondary device as a basis for adapting functions and settings in the secondary device to provide personalized usage of the secondary device by the first user.

According to another aspect, an arrangement is provided in a secondary device operable for enabling personalized usage of the secondary device by a first user of a first primary device. The arrangement in the secondary device comprises a communication module configured to send triangulation information to the first primary device as a basis for determining whether the secondary device is located within said limited area. The triangulation information comprises signal strength measurements performed by the secondary device of signals transmitted from a set of devices associated with the first primary device and forming a limited area of proximity to the first primary device.

The communication module is also configured to establish, when the secondary device is located within the limited area, a connection with the first primary device, and to receive identity information of the first user from the first primary device. The arrangement in the secondary device further comprises an adaptation module configured to adapt functions and settings in the secondary device, based on the received identity information of the first user, to provide personalized usage of the secondary device by the first user.

An advantage with the above solution is that the secondary device can be automatically adapted for personal usage by the first user when it is located close to the user's primary device, i.e. when determined to be within the limited area. Moreover, this solution does not require a mechanism and procedure in the secondary device for login or the like, and any security in terms of user authentication and so forth provided for the primary device can be utilized when personalizing the secondary device as well.

The above methods and arrangements may be configured and implemented according to different optional embodiments. In one possible embodiment, the first primary device determines whether the secondary device is located within said limited area further based on triangulation information with signal strength measurements received from the associated devices. Thereby, the secondary device's position relative to the limited area may be determined with further accuracy. In another embodiment, the first primary device may establish the connection with the secondary device by using a pairing procedure, which many devices are normally configured to employ for short range communication.

In another possible embodiment, the secondary device may be configured to further enable personalized usage of the secondary device by a second user of a second primary device, as follows. The secondary device may release adaptation to the first user from the secondary device when the secondary device moves out of the limited area of proximity to the first primary device. The secondary device may then send triangulation information to the second primary device, which comprises signal strength measurements of signals transmitted from another set of devices associated with the second primary device and forming a limited area of proximity to the second primary device, as a basis for determining whether the secondary device is located within the latter limited area.

When located within that limited area, the secondary device also establishes a connection with the second primary device and receives identity information of the second user from the second primary device. Thereby, functions and settings can be adapted in the secondary device based on the received identity information of the second user, to provide personalized usage of the secondary device by the second user.

In further possible embodiments, the connection with the first or second primary device can be established over a short range wireless connection involving any of: Bluetooth, Infrared, Near Field Connection (NFC), Wireless USB, WIFI, and Low-Rate Wireless Personal Area Networks. Further, adapting functions and settings in the secondary device to the first or second user may include retrieving personalized information from a central server or from a local storage in the secondary device.

In another possible embodiment, the first or second primary device can be identified/recognized based on a predefined list of primary devices configured in the secondary device, before the connection with the first or second primary device is established. For example, at least one of the first or second primary device may be a mobile phone and the secondary device may be any of: a camera, a media player, a portable computer, a game console, a vehicle control unit and a physical monitoring unit. The solution is however not limited to these examples but can be used for any types of primary and secondary devices capable of short range communication.

If further security or usefulness is desired, the first or second user may be prompted by the secondary device to verify or acknowledge himself as a user of the first or second primary device, respectively, before the functions and settings in the secondary device are adapted for personalized usage.

Further possible features and benefits of this solution will become apparent from the detailed description below.

BRIEF DESCRIPTION OF DRAWINGS

The invention will now be described in more detail by means of exemplary embodiments and with reference to the accompanying drawings, in which.

DETAILED DESCRIPTION

Briefly described, a solution is provided to enable personalized usage of a secondary device by a user of a primary device, as follows. In this description, the term "primary device" is thus used to represent any terminal or device being associated with a particular user who can be identified by identity information, and a "secondary device" represents any terminal or device which can be adapted to a user for personalized usage. It is assumed that both devices are capable of wireless short-range communication e.g. based on Bluetooth, Infrared, Near Field Connection (NFC), Wireless USB, WIFI, or Low-Rate Wireless Personal Area Networks. The solution is however not limited to any particular standard or technique for wireless short-range communication.

In practice, the primary device may be a mobile phone typically providing strong security for authenticating its user in a mobile network, e.g. based on a Subscriber Identity Module (SIM), while the secondary device may be, without limiting this solution, a camera, a media player, a portable computer, a game console, a tablet, a mobile phone, a vehicle control unit or a physical monitoring unit.

The primary device first detects when the secondary device has moved into a limited area of proximity around the primary device, which area is defined by a set of other devices associated with the primary device and which are likewise capable of wireless short-range communication. These associated devices are thus connected to the primary device by means of wireless short range connections and form a limited area jointly with the primary device, such as a sphere or other freely defined space, within which the presence of the entering secondary device can be detected by means of triangulation calculations, which will be described in more detail below.

When the secondary device is determined to be located within the limited area, the primary device establishes a connection and sends identity information of the first user to the secondary device. The secondary device can then use the received identity information as a basis for adapting its functions and settings to the first user, e.g. by retrieving personalized information from a central server and/or from a local storage in the secondary device, in order to provide personalized usage of the secondary device by the user.

In this way, the secondary device will be adapted for personal usage automatically when in proximity to the user's primary device, without requiring a mechanism and procedure for login or the like. In particular, if the primary device is a mobile phone the user is authenticated and/or registered as a valid subscriber in a mobile network, e.g. based on a SIM in the phone, which will provide ample and strong security against intruders. For example, personalized usage may entail that no other user than the allowed user is able to activate and use the secondary device at all. Optionally, the user may be prompted to verify or acknowledge himself as a user of the primary device before the functions and settings are adapted for personalized usage of the secondary device, thus bringing further security.

Figure 2:
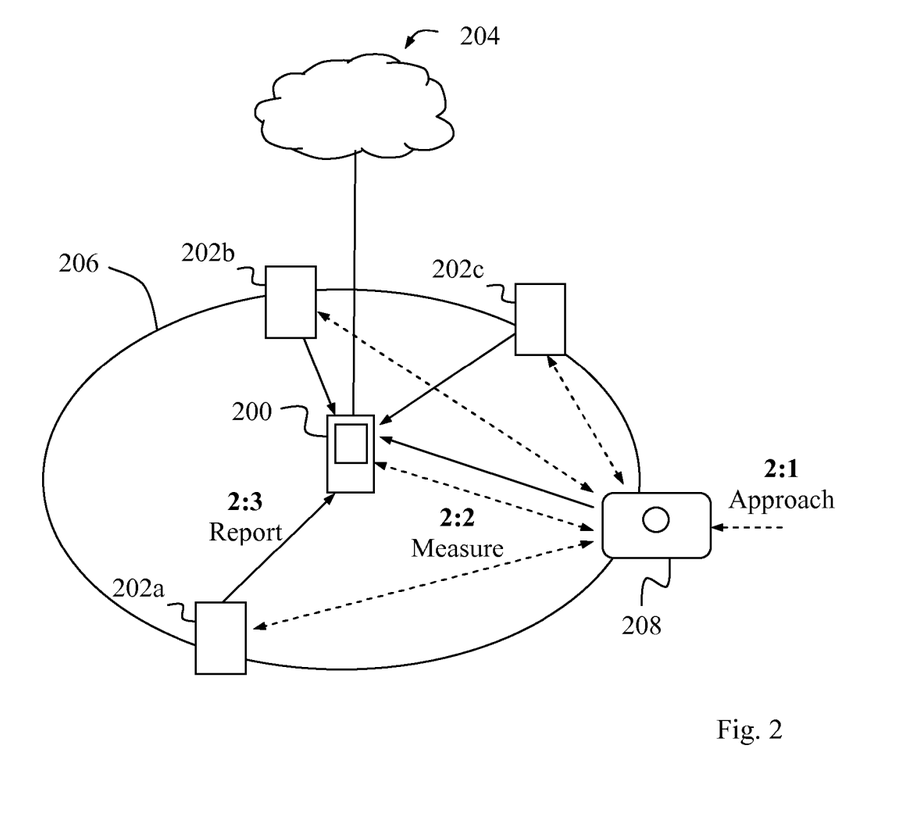
FIG. 2 is a communication overview illustrating how a secondary device can be detected as being close to a primary device, according to a possible embodiment.

FIG. 2 illustrates how the presence of a secondary device can be detected by means of triangulation calculations. A primary device 200 owned or controlled by a particular user, here called "first user", has a set of associated devices 202a, 202b, 202c which form, jointly with the primary device 200, a limited area or space 206 which is defined as an "area of proximity" to the first primary device. The size of this area 206 may basically be defined by received signal strengths of signals transmitted to and/or from the devices 200, 202a-c, knowing the transmit power used, such that it can be determined whether a "visiting" device is within the area or not by measuring received signal strengths to and/or from the devices 200, 202a-c.

It is assumed that the associated devices 202a-c are likewise owned or controlled by the first user and are located relatively close to this user and his primary device 200, i.e. at least within reach for wireless short-range communication. It should be noted that even though three associated devices are shown in this example, any number of associated devices may be used and the solution is not limited in this respect. The primary device 200, e.g. a mobile phone, is also registered with a mobile network 204, thus providing good security as described above.

In this example, the first user gets hold of a camera 208 capable of wireless short-range communication such as Bluetooth, Infrared, NFC, Wireless USB, WIFI, or Low-Rate Wireless Personal Area Networks, and brings it within the limited area 206 where the camera can act as a "visiting" secondary device as follows. Here, the camera 208 is thus synonymous with a secondary device. When the camera 208 approaches the area 206, shown as an action 2:1, it measures the signal strength of signals transmitted from the devices 200 and 202a-c, shown as dashed two-way arrows in another action 2:2. Likewise, devices 200 and 202a-c may also perform signal strength measurements on each other and the approaching camera 208 in this action.

The camera 208, i.e. secondary device, as well as the other devices 202a-c then send reports with the resulting signal strength measurements to the primary device 200, shown as full one-way arrows in an action 2:3. These measurement reports effectively contain triangulation information which the primary device 200 can use as a basis for estimating the relative position of the camera 208 and for determining whether it is located within the limited area 206 or not. In this description, the term "triangulation information" represents any signal measurements from which a device's position can be calculated using a suitable triangulation procedure.

Generally, such signal measurements may be triggered in different ways, depending on the communication protocol used. For example, the primary device 200 may be configured to frequently send out a measurement request, e.g. once a second, that can be received by any device within reach to hear it. This request may contain a list of associated devices, in this case devices 202a-c, on which signal measurements should be made and be reported to the primary device. Alternatively, the secondary device may be configured to frequently send out a suitable signal, such as a so-called "keep-alive timer" which is normally used for maintaining a short-range connection, i.e. "keeping in touch", and for detecting when a device goes out of reach. When hearing this signal from an approaching secondary device, in this case the camera 208, the primary device 200 may be configured to issue a request for signal measurements to that device and optionally to the associated devices 202a-c as well.

In either case, the primary device 200 and its associated devices 202a-c may thus likewise be triggered to perform signal measurements on each other and on the approaching secondary device. Thereby, the relative position of the secondary device 208 can be determined by triangulation calculations based on the signal measurements performed and reported by at least the secondary device 208, and optionally also by the devices 200 and 202a-c if greater accuracy is desired. The signal measurements and triangulation calculations as such can be performed according to regular procedures which are not necessary to described here in more detail to understand the present solution.

Figure 3:
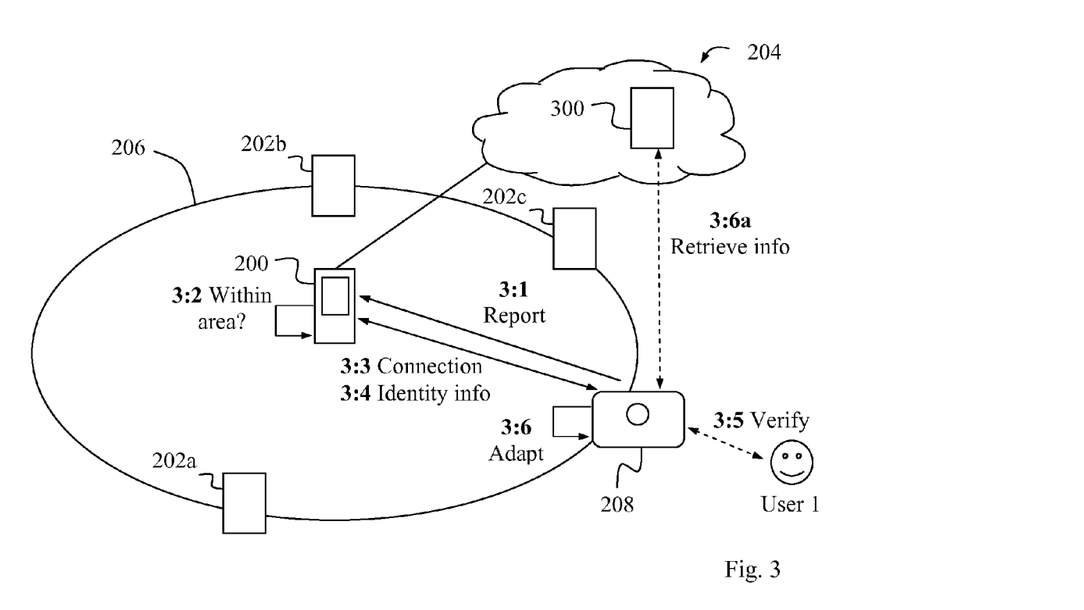
FIG. 3 is a communication overview illustrating how a secondary device can be detected to be close to a primary device, according to a possible embodiment.

FIG. 3 basically shows a continuation from FIG. 2 and illustrates how the camera 208 can be adapted for personalized use by the first user once it is determined to be present within the area 206 based on the reported signal measurements, i.e. the triangulation information received by the primary device 200 in action 2:3 above. The report from the camera 208 made in action 2:3 is shown here as an action 3:1 although such measurement reports may further be received from the other devices as well, not shown in this figure. In a next action 3:2, the primary device 200 determines whether the camera 208 is located within the limited area 206 based on the triangulation information received at least from the camera 208 but preferably also from the other devices 202a-c, which are thus not shown here for simplicity.

Having moved in relatively close to the primary device 200, the camera 208 is determined to be located within the area 206 and a connection is established between the primary device 200 and the camera in an action 3:3. This connection may involve a regular so-called "pairing" procedure which is normally employed in short-range communication between two devices e.g. for exchanging identities and capabilities to enable communication of data and media. In an optional embodiment, the camera 208 may have been configured with a predefined list of primary devices which are owned or controlled by known potential and on beforehand allowed users of the camera 208. The camera is thereby able to identify/recognize the primary device 200 as being owned by a known and allowed user 1 if present in the predefined list, before establishing a connection with the primary device.

The primary device 200 then sends information to the camera 208 regarding the identity of the first user, in an action 3:4, which the latter can use as a basis for adapting functions and settings in the camera to provide personalized usage of the secondary device by the first user. Before that, the camera 208 may prompt the first user is to verify or acknowledge himself as the user/owner of the primary device 200, as shown in an optional action 3:5, before adapting functions and settings in the camera for personalized usage. In this regard, the camera 208 may be configured in different ways, either to prompt the user for verification or to make the adaptation automatically without involving the user. The camera 208 may further be configured to allow any number of predefined users, e.g. according to a list as said above, or just one particular user.

The camera 208 then adapts one or more functions and settings to user 1 in the camera in an action 3:6, based on the received identity information of the first user. This action may include retrieving personalized information on preferences and requirements regarding the functions and settings, which may be maintained in a local storage in the camera and/or in a central server 300 in the network 204 where the user 1 is a registered subscriber. The personalized information may thus be retrieved locally in the camera 208, or from the central server 300 as illustrated by a complementary action 3:6a, or both.

Figure 4:
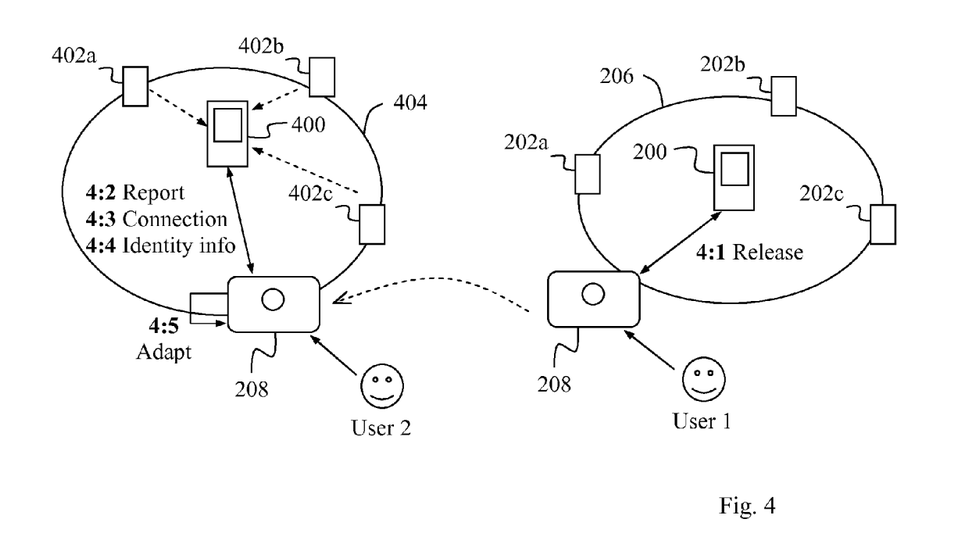
FIG. 4 is a communication overview illustrating how a secondary device can be detected to be close to a primary device, according to a possible embodiment.

The camera 208 is now adapted for personalized usage by the first user. In further possible embodiments, the camera 208 may at some point later be handed over to another user "2", where the above procedure for personalized use can be repeated as illustrated in FIG. 4 which may be seen as a continuation of FIG. 3. In the following, the primary device 200 of user 1 will be referred to as the first primary device while user 2 owns or controls a second primary device 400 which likewise has a set of associated devices 402a, 402b and 402c which jointly define another limited area 404 in which the presence of a visiting device can be detected in a manner similar to the procedure of FIGS. 2 and 3 above.

In this example, the second user 2 picks up the camera 208 from user 1 which results in that the camera moves out of the area 206 which may be detected by the first primary device 200 e.g. using further signal measurements on the camera 208 performed by one or more of the devices 200 and 202a-c. A first action 4:1 in FIG. 4 illustrates that the first primary device 200 releases the current adaptation to the first user from the camera 208 when it moves out of the limited area 206 of proximity to the first primary device 200, e.g. by sending a suitable adaptation release message to the camera 208. Alternatively, the camera 208 may by itself decide to release its current adaptation to the first user when detecting that it has moved out of the area 206, e.g. when the signal strength from one or more of devices 200 and 202a-c falls below a preset threshold or disappears altogether.

When picked up by the second user, the camera 208 approaches and enters the area 404 and accordingly performs measurements on signals from devices 400 and 402a-c and send reports with the resulting signal measurements to the second primary device 400, in an action 4:2. Signal measurements may also be performed and reported by the other devices 402a-c as well, basically in the manner described for FIG. 2 and schematically illustrated by dashed arrows. These measurement reports effectively contain triangulation information which the primary device 400 can use as a basis for estimating the relative position of the camera 208 and for determining whether it is located within the limited area 404 or not, just as described above when the camera approached and entered area 206.

The following procedure of establishing a connection between devices 400 and 208 in action 4:3, conveying identity information of user 2 to camera 208 in action 4:3, and accordingly adapting the camera 208 in action 4:5 are performed in basically the same manner as in actions 3:3-3:6 above and will therefore not be described in detail again here. In this way, a secondary device, in this example the camera 208, can easily be adapted to different users for personalized usage simply by locating it close to a primary device owned and controlled by each user. As said above, the secondary device may be pre-configured to allow personal adaptation only to a limited predefined set of users or even to just one particular user.

Figure 5:
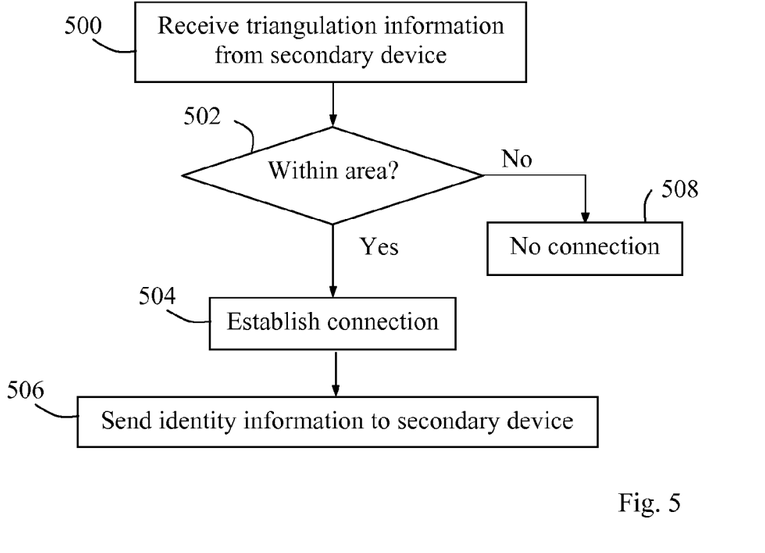
FIG. 5 is a flow chart illustrating a procedure in a primary device, according to further possible embodiments.

The solution described above by means of the examples shown in FIGS. 2-4 can be implemented as actions in the primary device and actions in the secondary device, which will now be described with reference to the flow charts in FIGS. 5 and 6, respectively. FIG. 5 thus illustrates a procedure in a first primary device for enabling personalized usage of a secondary device by a first user of the first primary device.

In a first action 500, the first primary device receives triangulation information from the secondary device, which comprises signal strength measurements by the secondary device of signals transmitted from a set of devices associated with the first primary device and forming a limited area of proximity to the first primary device, basically corresponding to actions 2:3 and 3:1 above.

In a next action 502, the first primary device determines whether the secondary device is located within the limited area based on the received triangulation information. If so, the first primary device establishes a connection with the secondary device in an action 504, and sends identity information of the first user to the secondary device in a further action 506. The identity information can then be used as a basis for adapting functions and settings in the secondary device to provide personalized usage of the secondary device by the first user. If the secondary device is determined not to be located within the limited area, no connection is established as shown in an alternative action 508 which thus falls outside this solution.

Figure 6:
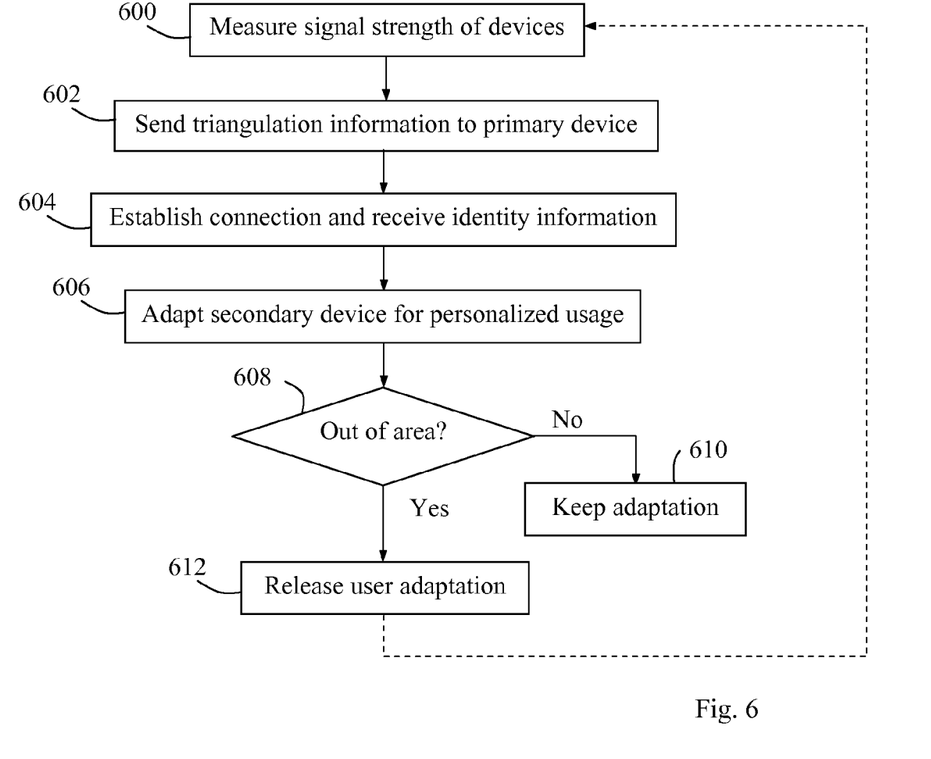
FIG. 6 is a flow chart illustrating a procedure in a secondary device, according to further possible embodiments.

FIG. 6 illustrates a procedure in a secondary device for enabling personalized usage of the secondary device by a first user of a first primary device, which devices correspond to the ones involved in FIG. 5. In a first action 600, the secondary device measures signals transmitted from a set of devices associated with the first primary device and forming a limited area of proximity to the first primary device, basically corresponding to action 2:2 above. The secondary device then sends triangulation information to the first primary device, in a further action 602, which comprises the signal strength measurements made in action 600, as a basis for determining whether the secondary device is located within said limited area.

When the first primary device has detected the secondary device to be located within the limited area, a connection is established with the first primary device and the secondary device receives identity information of the first user from the first primary device, in a further action 604. Thereby, the secondary device is able to adapt its functions and settings based on the received identity information of the first user, in a further action 606, to provide personalized usage of the secondary device by the first user.

The shown procedure also comprises an action 608 of determining whether the secondary device has moved out of the area of proximity to the first primary device. If still in the area, the secondary device keeps the adaptation to the first user made in action 606 for the time being, as illustrated in a schematic block 610. If determined to have moved out of the area, the secondary device releases the adaptation to the first user, in a final shown action 612, assuming that the first user no longer uses the secondary device.

If for example the secondary device at some point is picked up by a second user of a second primary device, and thereby approaches an area of proximity to a second primary device likewise formed by a set of associated devices, the process may return to action 600 as indicated by a dashed arrow, for repeating the above-described procedure with respect to the second primary device. This change of users thus corresponds to the scenario of FIG. 4 described above.

Figure 7:
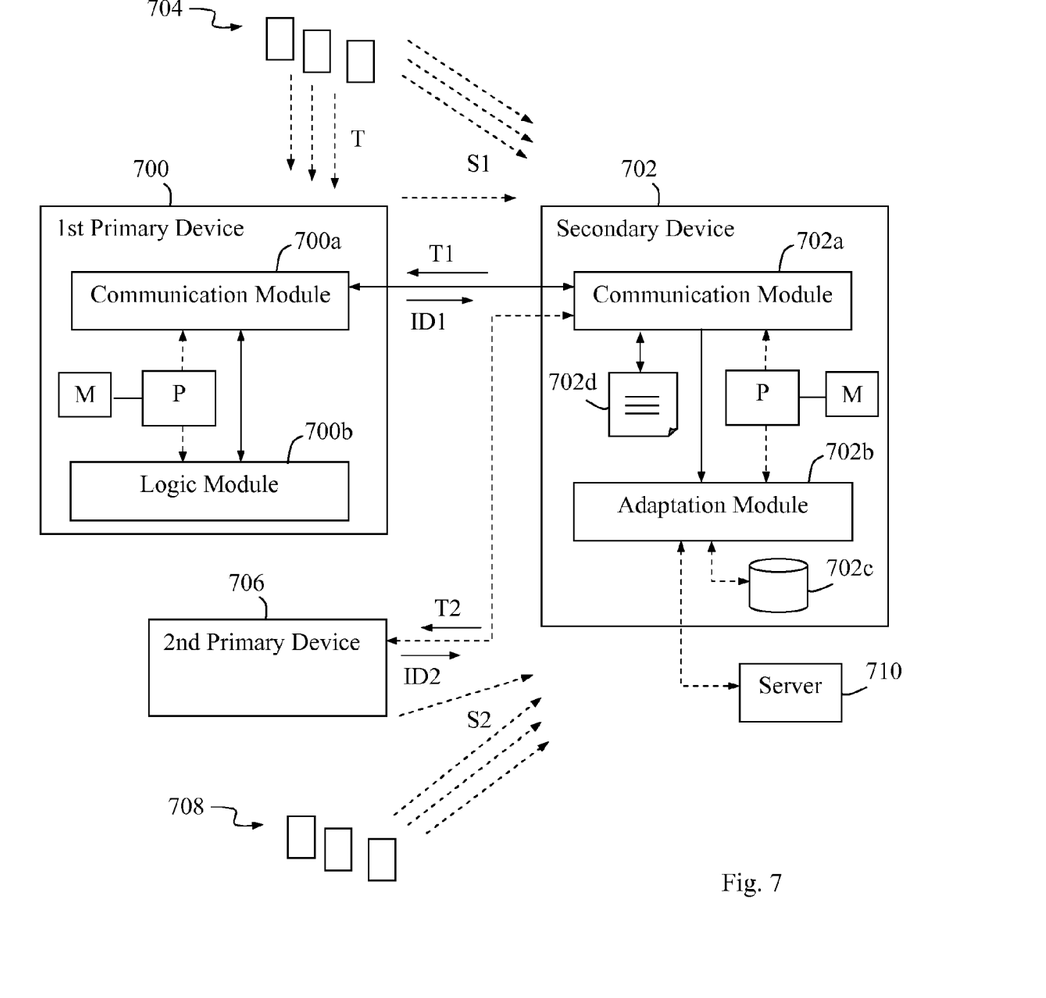
FIG. 7 is a block diagram illustrating examples of a primary device and a secondary device in more detail, according to further possible embodiments.

A detailed but non-limiting example of how a primary device and a secondary device can be configured to accomplish the above-described solution, is illustrated by the block diagram in FIG. 7. The primary device 700 is thus used and/or owned by a first user which can bring the secondary device 702 close to the primary device 700 for automatic personalization of the secondary device 702, e.g. in the manner described above for any of FIGS. 2-6.

FIG. 7 thus discloses an arrangement in the first primary device 700 operable for enabling personalized usage of the secondary device 702 by a user of the first primary device. According to this arrangement, the first primary device 700 comprises a communication module 700a configured to receive triangulation information "T1" from the secondary device. The triangulation information T1 comprises signal strength measurements made by the secondary device of signals "S1" transmitted from at least a set of devices 704 associated with the first primary device 700 and forming a limited area of proximity to the first primary device, optionally also of signals transmitted from the first primary device 700, e.g. in the manner described for FIG. 2 above. Module 700a may also receive further triangulation information "T" from the associated devices 704 with signal strength measurements of signals from at least the secondary device 702.

The first primary device 700 also comprises a logic module 700b configured to determine whether the secondary device 702 is located within the limited area based on the received triangulation information T1. The communication module 700a is further configured to establish a connection with the secondary device when determined to be located within the limited area, and to send identity information "ID1" of the first user to the secondary device as a basis for adapting functions and settings in the secondary device to provide personalized usage of the secondary device by the first user.

The above first primary device 700 and its functional modules 700a and 700b may be configured or adapted to operate according to various optional embodiments. For example, the logic module 700b may in one embodiment be configured to determine whether the secondary device is located within the limited area further based on the triangulation information T with signal strength measurements received from the associated devices 704 as well. In another possible embodiment, the communication module 700a is further configured to establish a connection with the secondary device in a pairing procedure, as described above.

FIG. 7 further discloses an arrangement in the secondary device 702 for enabling personalized usage of the secondary device by the first user of the first primary device 700. According to this arrangement, the secondary device 702 comprises a communication module 702a configured to send triangulation information T1 to the first primary device. The triangulation information T1 comprises signal strength measurements made by the secondary device of signals S1 transmitted from a set of devices 704 associated with the first primary device and forming a limited area of proximity to the first primary device. The triangulation information T1 from the secondary device 702, and optionally also the triangulation information T from the associated devices 704, can then be used by the first primary device 700 as a basis for determining whether the secondary device 702 is located within the limited area.

The communication module 702a is also configured to establish, when located within the limited area, a connection with the first primary device 700, and to receive identity information ID1 of the first user from the first primary device. The secondary device 702 also comprises an adaptation module 702b configured to adapt functions and settings in the secondary device, based on the received identity information ID1 of the first user, to provide personalized usage of the secondary device by the first user.

The above secondary device 702 and its functional modules 702a and 702b may also be configured or adapted to operate according to various optional embodiments. For example, the secondary device 702 may in an embodiment be further operable for enabling personalized usage of the secondary device by a second user of a second primary device 706. In that case, the adaptation module 702b may be further configured to release adaptation to the first user from the secondary device when the secondary device moves out of said limited area of proximity to the first primary device.

Also, the communication module 702a is in this case further configured to send triangulation information "T2" to the second primary device 706. The triangulation information T2 comprises signal strength measurements of signals "S2" transmitted from a set of devices 708 associated with the second primary device 706 and forming a limited area of proximity to the second primary device, as a basis for determining whether the secondary device is located within said limited area. Further, the communication module 702a is in this case also configured to establish, when located within the limited area, a connection with the second primary device 706, illustrated by a dashed two-way arrow, and to receive identity information "ID2" of the second user from the second primary device 706. The adaptation module 702b is in this case further configured to adapt functions and settings in the secondary device, based on the received identity information ID2 of the second user, to provide personalized usage of the secondary device by the second user.

In further possible embodiments, the communication module 702a may be configured to establish the connection with the first or second primary device over a short range wireless connection involving any of: Bluetooth, Infrared, NFC, Wireless USB, WIFI, and Low-Rate Wireless Personal Area Networks. Adapting functions and settings in the secondary device to the first or second user may further include retrieving personalized information from a central server 710 or from a local storage 702c in the secondary device.

The communication module 702a may be further configured to identify/recognize the first or second primary device based on a predefined list 702d of primary devices configured in the secondary device, before establishing the connection with the first or second primary device. For example, at least one of the first or second primary device may be a mobile phone and the secondary device may be any of: a camera, a media player, a portable computer, a game console, a vehicle control unit and a physical monitoring unit, without limitation to these examples. If additional security or privacy is desirable, the adaptation module 702b may be further configured to prompt the first or second user to verify or acknowledge himself as a user of the first or second primary device, respectively, before adapting functions and settings in the secondary device for personalized usage.

It should be noted that FIG. 7 merely illustrates various functional modules or units in the primary device 700 and the secondary device 702 in a logical sense, although the skilled person is free to implement these functions in practice using suitable software and hardware means. Thus, this aspect of the solution is generally not limited to the shown structures of the primary device 700 and the secondary device 702, while their respective functional modules 700a-b and 702a-b may be configured to operate according to the features described for any of FIGS. 2-6 above, where appropriate.

The functional modules 700a-b and 702a-b described above can be implemented in the primary device 700 and the secondary device 702, respectively, as program modules of a respective computer program comprising code means which, when run by a processor "P" in each of the primary device 700 and the secondary device 702 causes them to perform the above-described actions. Each processor P may be a single Central Processing Unit (CPU), or could comprise two or more processing units. For example, the processor P may include general purpose microprocessors, instruction set processors and/or related chips sets and/or special purpose microprocessors such as Application Specific Integrated Circuits (ASICs). The processor P may also comprise a storage for caching purposes.

Each computer program may be carried by a computer program product in either of the primary device 700 and the secondary device 702, respectively, in the form of a memory "M" connected to each processor P. The computer program product or memory M comprises a computer readable medium on which the computer program is stored. For example, the memory M may be a flash memory, a Random-Access Memory (RAM), a Read-Only Memory (ROM) or an Electrically Erasable Programmable ROM (EEPROM), and the program modules could in alternative embodiments be distributed on different computer program products in the form of memories within the primary device 700 and the secondary device 702.

While the invention has been described with reference to specific exemplary embodiments, the description is generally only intended to illustrate the inventive concept and should not be taken as limiting the scope of the invention. For example, the terms "device", "personalized usage", "identity information", "triangulation information", and "short range wireless connection" have been used throughout this description, although any other corresponding nodes, functions, and/or parameters could also be used having the features and characteristics described here. The invention is defined by the appended claims.

The invention claimed is:

1. A method in a first primary device for enabling personalized usage of a secondary device by a first user of the first primary device, the method comprising:
   receiving triangulation information from the secondary device, the triangulation information comprising signal strength measurements by the secondary device of signals transmitted from a set of devices associated with the first primary device and forming a limited area of proximity to the first primary device;
   determining whether the secondary device is located within said limited area based on the received triangulation information;
   establishing a connection with the secondary device when determined to be located within the limited area; and
   sending identity information of the first user to the secondary device as a basis for adapting functions and settings in the secondary device to provide personalized usage of the secondary device by the first user, wherein personalized usage comprises the secondary device being adapted for a specific user or owner in the way the device functions or operates, or both;
   wherein the first primary device is identified based on a predefined list of primary devices configured in the secondary device, before establishing connection with the secondary device.

2. The method of claim 1, wherein determining whether the secondary device is located within said limited area is further based on triangulation information with signal strength measurements received from the associated devices.

3. The method of claim 1, wherein establishing a connection with the secondary device includes a pairing procedure.

4. A method in a secondary device for enabling personalized usage of the secondary device by a first user of a first primary device, the method comprising:
   sending triangulation information to the first primary device, the triangulation information comprising signal strength measurements by the secondary device of signals transmitted from a set of devices associated with the first primary device and forming a limited area of proximity to the first primary device, as a basis for determining whether the secondary device is located within said limited area;

establishing, when located within the limited area and based on the identification of the first primary device, a connection with the first primary device;

receiving identity information of the first user from the first primary device; and adapting functions and settings in the secondary device, based on the received identity information of the first user, to provide personalized usage of the secondary device by the first user, wherein personalized usage comprises the secondary device being adapted for a specific user or owner in the way the device functions or operates, or both;

wherein the first primary device is identified based on a predefined list of primary devices configured in the secondary device, before establishing connection with the first primary device.

5. The method of claim 4, further enabling personalized usage of the secondary device by a second user of a second primary device, the method further comprising:

releasing adaptation to the first user from the secondary device when the secondary device moves out of said limited area of proximity to the first primary device;

sending triangulation information to the second primary device, the triangulation information comprising signal strength measurements of signals transmitted from a set of devices associated with the second primary device and forming a limited area of proximity to the second primary device, as a basis for determining whether the secondary device is located within said limited area;

establishing, when located within the limited area, a connection with the second primary device;

receiving identity information of the second user from the second primary device; and adapting functions and settings in the secondary device, based on the received identity information of the second user, to provide personalized usage of the secondary device by the second user.

6. The method of claim 5, wherein the connection is established with the first or second primary device over a short range wireless connection involving any of: Bluetooth, Infrared, Near Field Connection (NFC), Wireless USB, WIFI, and Low-Rate Wireless Personal Area Networks.

7. The method of claim 5, wherein adapting functions and settings in the secondary device to the first or second user includes retrieving personalized information from a central server or from a local storage in the secondary device.

8. The method of claim 5, wherein the second primary device is identified based on a predefined list of primary devices configured in the secondary device, before establishing connection with the second primary device.

9. The method of claim 5, wherein at least one of the first or second primary device is a mobile phone and the secondary device is any of: a camera, a media player, a portable computer, a game console, a vehicle control unit and a physical monitoring unit.

10. The method of claim 5, wherein the first or second user is prompted to verify himself as a user of the first or second primary device, respectively, before functions and settings are adapted in the secondary device for personalized usage.

11. An arrangement in a first primary device operable for enabling personalized usage of a secondary device by a first user of the first primary device, the arrangement comprising:

a communication circuit configured to receive triangulation information from the secondary device, the triangulation information comprising signal strength measurements by the secondary device of signals transmitted from a set of devices associated with the first primary device and forming a limited area of proximity to the first primary device;

a logic circuit configured to determine whether the secondary device is located within said limited area, based on the received triangulation information; and the communication circuit being further configured to:
establish a connection with the secondary device when determined to be located within the limited area, and to send identity information of the first user to the secondary device as a basis for adapting functions and settings in the secondary device to provide personalized usage of the secondary device by the first user, wherein personalized usage comprises the device being adapted for a specific user or owner in the way the device functions or operates, or both;

wherein the first primary device is identified based on a predefined list of primary devices configured in the secondary device, before establishing connection with the secondary device.

12. The arrangement of claim 11, wherein the logic circuit is further configured to determine whether the secondary device is located within said limited area further based on triangulation information with signal strength measurements received from the associated devices.

13. The arrangement of claim 11, wherein the communication circuit is further configured to establish a connection with the secondary device in a pairing procedure.

14. An arrangement in a secondary device operable for enabling personalized usage of the secondary device by a first user of a first primary device, the arrangement comprising:

a communication circuit configured to send triangulation information to the first primary device, the triangulation information comprising signal strength measurements by the secondary device of signals transmitted from a set of devices associated with the first primary device and forming a limited area of proximity to the first primary device, as a basis for determining whether the secondary device is located within said limited area;

the communication circuit being also configured to identify the first primary device based on a predefined list of primary devices configured in the secondary device, establish, based on the identification of the first primary device and when located within the limited area, a connection with the first primary device, and to receive identity information of the first user from the first primary device; and an adaptation circuit configured to adapt functions and settings in the secondary device, based on the received identity information of the first user, to provide personalized usage of the secondary device by the first user, wherein personalized usage comprises the secondary device being adapted for a specific user or owner in the way the device functions or operates, or both.

15. The arrangement of claim 14, further operable for enabling personalized usage of the secondary device by a second user of a second primary device, wherein:

the adaptation circuit is further configured to release adaptation to the first user from the secondary device when the secondary device moves out of said limited area of proximity to the first primary device, the communication circuit is further configured to send triangulation information to the second primary device, the triangulation information comprising signal strength measurements of signals transmitted from a set of devices associated with the second primary device and forming a limited area of proximity to the second primary device, as a basis for determining whether the secondary device is located within said limited area, the communication circuit being also configured to establish, when located within the limited area, a connection with the second primary device, and to receive identity information of the second user from the second primary device, and the adaptation circuit is further configured to adapt functions and settings in the secondary device, based on the received identity information of the second user, to provide personalized usage of the secondary device by the second user.

16. The arrangement of claim 15, wherein the communication circuit is further configured to establish the connection with the first or second primary device over a short range wireless connection involving any of: Bluetooth, Infrared, Near Field Connection (NFC), Wireless USB, WIFI, and Low-Rate Wireless Personal Area Networks.

17. The arrangement of claim 15, wherein adapting functions and settings in the secondary device to the first or second user includes retrieving personalized information from a central server or from a local storage in the secondary device.

18. The arrangement of claim 15, wherein the communication circuit is further configured to identify the second primary device based on a predefined list of primary devices configured in the secondary device, before establishing connection with the second primary device.

19. The arrangement of claim 15, wherein at least one of the first or second primary device is a mobile phone and the secondary device is any of: a camera, a media player, a portable computer, a game console, a vehicle control unit and a physical monitoring unit.

20. The arrangement of claim 15, wherein the adaptation circuit is further configured to prompt the first or second user to verify himself as a user of the first or second primary device, respectively, before adapting functions and settings in the secondary device for personalized usage.

* * * * *